United States Patent [19]

Ichikawa et al.

[11] 4,164,462

[45] Aug. 14, 1979

[54] OXYGEN SENSOR

[75] Inventors: Norio Ichikawa, Mito; Kanemasa Sato; Sadayasu Ueno, both of Katsuta, all of Japan

[73] Assignee: Hitachi, Ltd., Tokyo, Japan

[21] Appl. No.: 855,325

[22] Filed: Nov. 28, 1977

[30] Foreign Application Priority Data

Nov. 29, 1976 [JP] Japan .................. 51-142250

[51] Int. Cl.$^2$ ............................................. G01N 27/58
[52] U.S. Cl. ................................................ 204/195 S
[58] Field of Search ............. 204/195 S, 1 S; 60/276; 123/119 E; 324/29

[56] References Cited

U.S. PATENT DOCUMENTS

| | | | |
|---|---|---|---|
| 3,843,400 | 10/1974 | Radford et al. | 204/195 S X |
| 3,978,006 | 8/1976 | Topp et al. | 252/477 R |
| 4,021,326 | 5/1977 | Pollner et al. | 204/195 S |
| 4,080,276 | 3/1978 | Bode | 204/195 S |

FOREIGN PATENT DOCUMENTS

| | | | |
|---|---|---|---|
| 49-63991 | 8/1974 | Japan | 204/195 S |
| 1201806 | 8/1970 | United Kingdom | 204/195 S |

OTHER PUBLICATIONS

Heinrich Dueker et al., Paper 750223, Soc. of Automotive Eng., Automotive Eng. Cong. & Exp., Feb. 24-28, 1975.

*Primary Examiner*—G. L. Kaplan
*Attorney, Agent, or Firm*—Craig and Antonelli

[57] ABSTRACT

A protective layer of zirconia particles having particle sizes of 0.5-5 $\mu M$ is provided on a surface of an electron-conducting layer of an oxygen sensor at a side of a gas whose oxygen concentration is to be detected to a thickness of 4-100 $\mu M$ by bonding zirconia particles to one another and the first electron-conducting layer by 10-30% by weight of a high melting point adhesive, such as powders of borosilicate glass, based on total weight of the zirconia particles.

5 Claims, 6 Drawing Figures

OXYGEN SENSOR

LIST OF PRIOR ART REFERENCES (37 CFR 1.56 (a))

The following references are cited to show the state of the art:

Society of Automotive Engineers, Automotive Engineering Congress and Exposition, Detroit, Mich., February 24–28, 1975, Paper 750223
U.S. Pat. No. 3,978,006
British Pat. No. 1201806
Japanese Laid-open Patent Specification No. 63991/75.

This invention relates to an oxygen sensor, and more particularly to an oxygen sensor suitable for an application to a gas at a very high temperature but in a rapid fluctuation, for example, for detecting an oxygen concentration of an exhaust gas from automobiles.

The so far well known oxygen sensor comprises a zirconia layer and electron-conducting layers having a catalytic action provided at both sides of the zirconia layer, where a gas whose oxygen concentration is to be detected, which will be hereinafter referred to as "exhaust gas", is contacted with the electron-conducting layer at one side, and a reference gas is contacted with the electron-conducting layer at the other side. When the exhaust gas is short of oxygen molecules in that case, oxygen molecules are converted to minus oxygen ions at the electron-conducting layer at the reference gas side, and the oxygen ions migrate towards the exhaust gas side through the zirconia layer. The oxygen ions discharge electrons at the electron-conducting layer at the exhaust gas side, and are converted to oxygen molecules. As a result, an electrical potential is developed between said two electron-conducting layers (Society of Automotive Engineers, Automotive Engineering Congress and Exposition, Detroit, Mich., February 24–28, 1975, Paper 750223).

When the exhaust gas contains various compounds or solid matters, there is a problem of deterioration of the electron-conducting layer at the exhaust gas side of the oxygen sensor. To prevent the deterioration, a porous protective layer has been provided on the electron-conducting layer at the exhaust gas side. As materials for the protective layer, for example, alloys of metals such as copper, nickel, chromium, etc., or borides, nitrides, silica materials, etc. have been proposed (U.S. Pat. No. 3,978,006; British Pat. No. 1201806; Japanese Laid-open Patent Specification No. 63991/75). However, porous protective layers made from said materials have a problem of durability. That is, when such porous protective layers are used in the oxygen sensor for detecting the oxygen concentration of the exhaust gas, there are problems of crack formation on the protective layer or deterioration in performance of the electron-conducting layer.

As a result of repetitions of experiments to investigate the causes for the problems, the present inventors have found that the problems are due to a difference in coefficients of thermal expansion between the zirconia layer transmitting the oxygen ions and the protective layer. That is, the oxygen sensor used as a sensor for the automobile exhaust gas is subject to thermal cycles, that is, the oxygen sensor is exposed, on one hand, to such a low temperature as below the ice point when the engine is off and, on the other hand, to such a high temperature as 900° C. within a short time when the engine is started. Furthermore, the engine is subject to repetitions of acceleration and speed reduction, and thus the temperature of the exhaust gas always fluctuates. Thus, the oxygen sensor is always subject to thermal shocks due to repetitions of expansion and contraction. If there is a difference in the coefficient of thermal expansion between the zirconia layer and the protective layer, stresses are concentrated on the protective layer or the electron-conducting layers, and the protective layer is finally damaged. Furthermore, the oxygen sensor is subject to vibrations of automobile body, which are increased with increasing acceleration. Such additional mechanical shock also causes the protective layer to be damaged.

An object of the present invention is to provide an oxygen sensor having a porous, but thin protective layer having a good durability.

According to the present invention, zirconia particles are used as a main component for the protective layer to minimize or almost eliminate the occurrence of stresses between the zirconia transmitting the oxygen ions and the protective layer, and the zirconia particles are bonded to one another by a small amount of an adhesive.

Now, the present invention will be described in detail, referring to the accompanying drawings.

Figure 1:
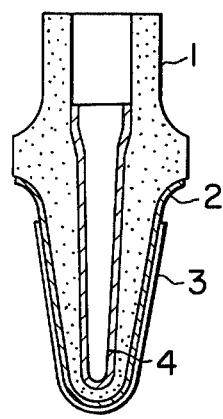
FIG. 1 is a cross-sectional view of the present oxygen sensor.

In FIG. 1, an electron-conducting layer 2 having a catalytic action is provided as an electrode at the outer surface of a zirconia layer 1 transmitting oxygen ions. The electron-conducting layer 2 is prepared by forming a porous platinum layer by vapor deposition, spattering, or thermal decomposition. Furthermore, another electron-conducting layer 4 is formed as an electrode on the inside surface of the zirconia layer 1 in the same manner as described above. The electron-conducting layers 2 and 4 are very thin, for example, several ten $\mu$M or less, but in FIG. 2 the electron-conducting layers 2 and 4 are depicted rather thick only for a ready comprehension purpose. A protective layer 3 is provided on the outer surface of the electron-conducting layer 2 to protect the zirconia layer 1 and the electrode 2 of the oxygen sensor from the exhaust gas. In the present embodiment, the zirconia layer 1 is a tube having a closed end, and atmospheric air is led to the inside of the tube as a reference gas, whereas the protective layer 3 is exposed to an exhaust gas as a gas whose oxygen concentration is to be detected. The exhaust gas is led to the electron-conducting layer 2 comprised of a platinum layer through numerous pores provided on the protective layer 3. Numerous pores having smaller sizes than those of the pores on the protective layer are provided on the platinum layer 2, providing such a structure as to make more ternary boundary interfaces consisting of faces of zirconia layer 1, platinum electrode 2 and the introduced exhaust gas.

When the oxygen molecules in the exhaust gas is less, the oxygen ions in the zirconia layer 1 discharge electrons to the electron-conducting layer 2 to form oxygen atoms or oxygen molecules, which generate at said ternary boundary interfaces. The generated oxygen atoms or molecules are combined with carbon monoxide, hydrocarbons, etc. in the exhaust gas by catalytic action of platinum, and are consumed, while oxygen molecules obtain electrons from the electron-conducting layer 4 at the reference gas side, and are converted to minus oxygen ions, which migrate towards the exhaust gas side through the zirconia layer 1. In this manner, an electrical potential develops between these two electron-conducting layers 2 and 4.

Various components, for example, CO, $O_2$, HC, $NO_x$, $H_2$, C, $H_2O$, Pb, S, and P are contained in an automobile exhaust gas, and among others carbon C, lead P, sulfur S, and phosphorus P are present as solid matters of large size.

Figure 2:
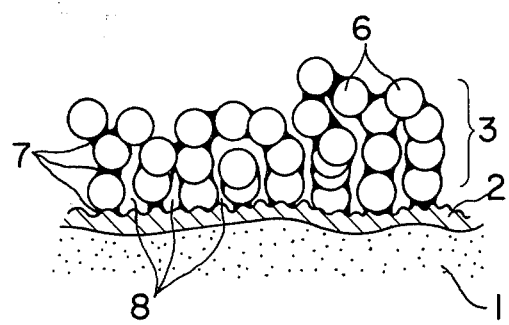
FIG. 2 is a schematic view showing a structure of a protective layer.

In FIG. 2, a protective layer of the present invention is schematically depicted, where a porous platinum layer 2 is formed on the surface of a zirconia layer 1, and zirconia particles 6 having particle sizes of 1-3 $\mu M$ are bonded to one another on the outer surface of the platinum layer 2 by a high melting point adhesive 7. A protective layer 3 is formed by bonding the zirconia particles 6. The thickness of the protective layer 3 is 4-100 $\mu M$, preferably 30 $\mu M$. If the protective layer 3 is thicker than 100 $\mu M$, a good response showing a feedback speed of the oxygen sensor cannot be obtained. If the protective layer is thinner than 4 $\mu M$, the function of protection of the protective layer is lost. Pores 8 formed by the zirconia particles can have different sizes, depending upon the particle sizes of the zirconia particles. As a result of experiments, the present inventors have found that pores 8 having the most suitable sizes (1-2 $\mu M$) can be obtained by using zirconia particles having particle sizes of 0.5-5 $\mu M$.

As described above, the exhaust gas contains various solid matters, and among the components of the exhaust gas only specific gases of small molecules, such as CO, $O_2$, $H_2$, etc. can pass through the pores 8 by the restriction of the sizes of pores 8, and passage of others can be prevented. Thus, the electron-conducting layer 2 and the zirconia layer 1 can be protected from various components in the exhaust gas by properly selecting the sizes of pores 8. To quicken the response ability as an oxygen sensor element, it is necessary to lead oxygen molecule $O_2$ or carbon monoxide molecule CO more quickly to the electron-conducting layer 2. Thus, more pores and their appropriate sizes are required in this sense. Furthermore, it is necessary to strongly fix the protective layer 3 to the electron-conducting layer 2, and thus it is necessary that the fixation strength be not lowered at a working temperature of the oxygen sensor, for example, not more than 900° C.

In bonding of zirconia particles 6 to one another and to the electron-conducting layer 2, too much adhesive fills up clearances 8 between the individual zirconia particles or pores on the electron-conducting layer 2, whereas too little adhesive fails to produce a good bonding strength. Thus, a preferable amount of adhesive is 10-30% by weight based on the total weight of the zirconia particles 6.

As the adhesive, for example, powders of borosilicate glass are used. That is 10-30% by weight of powders of borosilicate glass are mixed with zirconia particles, and the resulting mixture is mixed with a dispersion containing 3 parts by weight of ethylcellulose and 100 parts by weight of terpineol in a ratio by weight of the dispersion to the powders of borosilicate glass being 1:1 under stirring to produce a paste. The resulting paste is applied to the electron-conducting layer 2 of the oxygen sensor, and calicined at about 1,000° C. to form a protective layer 3.

As other adhesives, for example, water glass prepared so as to have a melting point of 900° C. or higher, aqueous solutions of phosphates such as aluminum phosphate and magnesium phosphate, cement, etc. are available. When the phosphate such as aluminum phosphate and magnesium phosphate is used, 10-30% by weight of the phosphate, based on the total weight of the zirconia particles, is mixed with the zirconia particles and prepared into a paste, and the resulting paste is applied to the electron-conducting layer, and calcined at 1,000° C. in the same manner as for said borosilicate glass.

Figure 3A:
FIG. 3(a) is an electron-microscopic picture of a state of a protective layer calcined at 1700° C. ($\times$500).

In FIG. 3(a), a protective layer 3 consisting only of zirconia particles, calcined at 1700° C., is shown, where the individual zirconia particles are fused, and the porosity is lost.

Figure 3B:
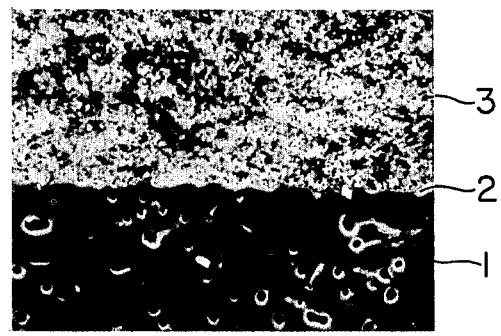
FIG. 3(b) is an electron-microscopic picture of a cross-section of a protective layer using aluminum phosphate as a high melting point adhesive ($\times$500).

In FIG. 3(b), a protective layer 3 prepared from the zirconia particles containing 20% by weight of aluminum phosphate is shown, where a good porosity is obtained.

Figure 3C:
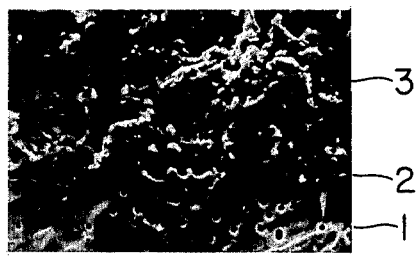
FIG. 3(c) is an electron-microscopic picture of a cross-section of a protective layer using borosilicate glass as a high melting point adhesive ($\times$500).

In FIG. 3(c), a protective layer 3 prepared from the zirconia particles containing 30% by weight of powders of borosilicate glass is shown, where a good porosity is obtained. Throughout FIGS. 3(a)-(c), numerals 1 and 2 are the zirconia layer and the electron-conducting layer, respectively, as defined before.

In these embodiments, zirconia layer 1 and the protective layer 3 have the same coefficients of thermal expansion, and thus there appears less strain due to changes in temperature between these two layers. The coefficient of thermal expansion of the adhesive is no problem, because the amount of the adhesive 7 is small. The bond between the electron-conducting layer 2 consisting of a platinum layer, and the protective layer 3 is attained by such a mechanical bond that the adhesive has partly entered into the pores on the platinum layer 2 and cured therein, and thus even if there is a great difference in the coefficients of thermal expansion between the platinum layer 2 and the protective layer 3, the strain due to the difference in the coefficients of thermal expansion can be absorbed by the pores of the platinum layer 2.

As described above, the zirconia particles are bonded to one another by a high melting point adhesive to form a protective layer. In that case, the zirconia particles used are those already stabilized by calcining them at a high temperature, for example, 1500° C. or higher, and thus only the adhesive is melted and flows through between the zirconia particles, whereas the zirconia particles themselves are hardly changed.

Figure 4:
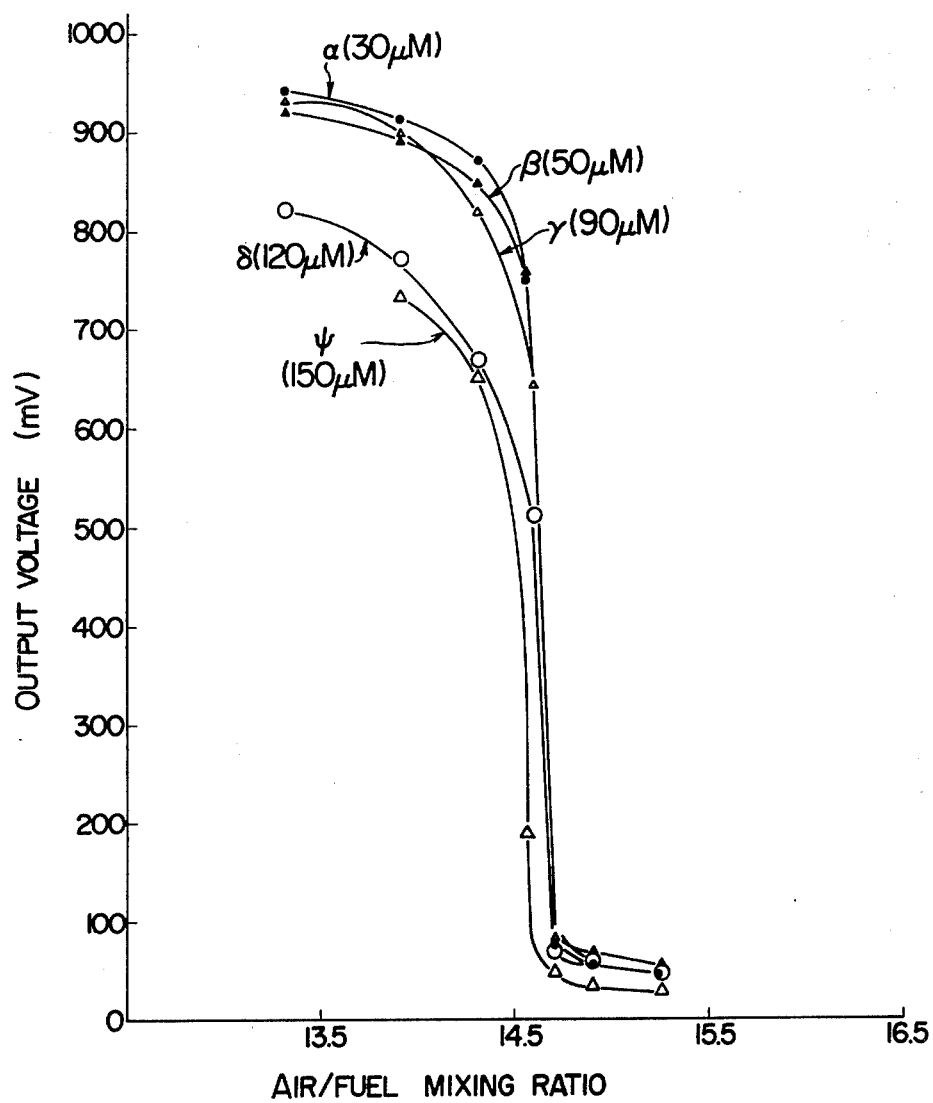
FIG. 4 is a diagram showing characteristics between output voltage and air/fuel mixing ratio by thickness of protective layer as a parameter.

In FIG. 4, output characteristics of the oxygen sensor when thickness of the protective layer is changed, is shown. With increasing thickness of the protective layer, the output voltage changes more roundly, and further, the output voltage is considerably lowered, if the thickness exceeds 100 $\mu M$. That is, the thickness of the protective layer is preferably not more than 10 $\mu M$. In the embodiments shown in FIG. 4, the protective layers prepared from zirconia particles (size: 2 μM) containing 30% by weight of powders of borosilicate glass with thickness 30 μM (α), 50 μM (β), 90 μM (γ), 120 μM (δ) and 150 μM (φ) were tested.

As described above, less strains develop between the zirconia layer and the protective layer, even if the temperature changes vigorously, and the durability of the oxygen sensor is considerably increased in the present invention.

What is claimed is:

1. An oxygen sensor, which comprises a zirconia layer for transmitting oxygen ions therethrough, provided to separate a gas whose oxygen concentration is to be detected from a reference gas; a first electron-conducting layer having a catalytic action, provided on a surface of the zirconia layer on the side of the gas whose oxygen concentration is to be detected; a second electron-conducting layer for ionizing oxygen molecules in the reference gas and taking the oxygen ions into the zirconia layer, provided on a surface of the zirconia layer on the side of the reference gas; and a protective layer of zirconia particles provided on the outer surface of the first electron-conducting layer, said zirconia particles being bonded to one another and to the first electron-conducting layer by a high melting point adhesive comprising a powder of borosilicate glass, water glass having a melting point of 900° C. or higher, a phosphate, or cement, whereby an electrical signal is generated between the first and the second electron-conducting layers in accordance with the difference in oxygen concentrations between the gas whose oxygen concentration is to be detected and the reference gas.

2. An oxygen sensor according to claim 1, wherein particle sizes of the zirconia particles for the protective layer are 0.5–5 μM.

3. An oxygen sensor according to claim 1, wherein thickness of the protective layer is 4–100 μM.

4. An oxygen sensor according to claim 1, wherein 10–30% by weight of the high melting point adhesive, based on total weight of the zirconia particle is used for the protective layer.

5. An oxygen sensor, which comprises a zirconia layer for transmitting oxygen ions therethrough, provided to separate a gas whose oxygen concentration is to be detected from a reference gas; a first electron-conducting layer having a catalytic action, provided on a surface of the zirconia layer on the side of the gas whose oxygen concentration is to be detected; a second electron-conducting layer for ionizing oxygen molecules in the reference gas and taking the oxygen ions into the zirconia layer, provided on a surface of the zirconia layer on the side of the reference gas; and a protective layer of zirconia particles having particle sizes of 0.5–5 μM to a thickness of 4–100 μM provided on the outer surface of the first electron-conducting layer, said zirconia particles being bonded to one another and to the first electron-conducting layer by 10–30% by weight of a high melting point adhesive, based on total weight of the zirconia particles, comprising a powder of borosilicate glass, water glass having a melting point of 900° C. or higher, a phosphate, or cement, whereby an electrical signal is generated between the first and second electron-conducting layers in accordance with a difference in oxygen concentration between the gas whose oxygen concentration is to be detected, and the reference gas.

* * * * *